(12) United States Patent
Dean

(10) Patent No.: US 11,642,029 B2
(45) Date of Patent: May 9, 2023

(54) METHODS AND DEVICES FOR ALLEVIATING DISORDERS ASSOCIATED WITH SINUS CAVITIES

(71) Applicant: Marc Richard Dean, Dallas, TX (US)

(72) Inventor: Marc Richard Dean, Dallas, TX (US)

( * ) Notice: Subject to any disclaimer, the term of this patent is extended or adjusted under 35 U.S.C. 154(b) by 0 days.

(21) Appl. No.: 17/157,821

(22) Filed: Jan. 25, 2021

(65) Prior Publication Data

US 2021/0228082 A1 Jul. 29, 2021

Related U.S. Application Data

(60) Provisional application No. 62/965,294, filed on Jan. 24, 2020.

(51) Int. Cl.
| | |
|---|---|
| *A61B 5/00* | (2006.01) |
| *A61B 17/24* | (2006.01) |
| *A61B 1/233* | (2006.01) |
| *A61B 17/16* | (2006.01) |
| *A61B 17/12* | (2006.01) |
| *A61B 1/05* | (2006.01) |
| *A61B 17/00* | (2006.01) |

(52) U.S. Cl.
CPC ............ *A61B 5/0053* (2013.01); *A61B 1/05* (2013.01); *A61B 1/233* (2013.01); *A61B 17/1204* (2013.01); *A61B 17/12099* (2013.01); *A61B 17/12136* (2013.01); *A61B 17/1688* (2013.01); *A61B 17/24* (2013.01); *A61B 2017/00044* (2013.01)

(58) Field of Classification Search
CPC .......................... A61B 17/1688; A61B 1/233
See application file for complete search history.

(56) References Cited

U.S. PATENT DOCUMENTS

| | | | | |
|---|---|---|---|---|
| 2005/0240147 A1* | 10/2005 | Makower | ............ | A61B 17/3201 604/96.01 |
| 2007/0208301 A1* | 9/2007 | Evard | .................... | A61M 29/02 604/103.1 |
| 2007/0269385 A1* | 11/2007 | Yun | .................... | A61K 31/7034 424/45 |

(Continued)

OTHER PUBLICATIONS

Stokovic et al., Sphenoid sinus types, dimensions and relationship with surrounding structures, Jan. 2016, Annals of Anatomy, vol. 203, pp. 69-76 (Year: 2016).*

(Continued)

*Primary Examiner* — Martin T Ton
(74) *Attorney, Agent, or Firm* — KPPB LLP

(57) ABSTRACT

Generally, abnormal pressures in the sinus cavity can have physiological effects due to stimulation or injury of various nerves that are in proximity to the sinus, including increased or decreased pressure on the nerves as well as extrusion of the nerves into the sinus cavities due to bony dehiscence. Methods and devices for alleviating disorders associated with the sinus cavities are described. Embodiments herein include diagnosing these disorders by occluding or restricting the sinus ostium and assessing the physiological effects caused by the occlusion/restriction and treating these disorders by navigating/directing a dilating device to the sinus ostium and dilating the sinus ostium. Other embodiments are directed to devices for maintaining the ostial opening.

30 Claims, 10 Drawing Sheets

(56) References Cited

U.S. PATENT DOCUMENTS

| | | | | |
|---|---|---|---|---|
| 2009/0036968 | A1* | 2/2009 | Hepworth | A61F 2/82 623/1.11 |
| 2010/0010564 | A1* | 1/2010 | Simon | A61N 1/0551 607/45 |
| 2010/0114191 | A1* | 5/2010 | Newman | A61N 7/00 607/3 |
| 2010/0241155 | A1* | 9/2010 | Chang | A61M 25/0068 606/196 |
| 2010/0274164 | A1* | 10/2010 | Juto | A61H 9/0078 601/46 |
| 2012/0330196 | A1* | 12/2012 | Nita | A61B 5/0036 601/2 |
| 2017/0360511 | A1* | 12/2017 | Smith | A61B 5/4824 |
| 2018/0000499 | A1* | 1/2018 | Altman | A61B 17/3421 |
| 2018/0318559 | A1* | 11/2018 | Becker | A61M 25/10 |
| 2019/0290314 | A1* | 9/2019 | Gemer | A61B 17/24 |
| 2019/0336765 | A1* | 11/2019 | Charlesworth | A61N 1/36034 |

OTHER PUBLICATIONS

Lawson et al., Isolated Sphenoid Sinus Disease: An Analysis of 132 Cases, 1977, The Laryngoscope, vol. 107 (Issue 12), pp. 1590-1595 (Year: 1977).*
Sawaya, Raja A., Trigeminal Neuralgia Associated with Sinusitis, ORL 2000; 62:160-163 (Year: 2000).*
DeCapua, Melissa, Chronic Sinusitis: A Review and Update, Dec. 28, 2017, Contemporary Clinic (Year: 2017).*
Illing et al., Outcomes of Pressure-Induced Cranial Neuropathies from Allergic Fungal Rhinosinusitis, Otolaryngology—Head Neck Surgery, 2015, vol. 152(3); 541-545 (Year: 2018).*
Andersson et al., "A Decrease in Maxillary Sinus Pressure, as Seen in Upper Airway Allergy or Infection, Results in an Increase in Upper Airway Nitric Oxide Levels", Acta Otolaryngologica, Jun. 30, 2002, vol. 122, No. 5, pp. 520-523, published online Jul. 8, 2009, DOI: 10.1080/00016480260092336.
Aust et al., "Basic Experimental Studies of Ostial Patency and Local Metabolic Environment of the Maxillary Sinus", Acta Otolaryngol. Suppl., 1994, vol. 515, pp. 7-11, doi: 10.3109/00016489409124315.
Hepworth, "Balloon Sinuplasty", Medscape, Dec. 9, 2020, 18 pgs.
Ivezic et al., "Resorption of gas trapped in the body cavities: comparison of alveolar and pleural space with inner ear and paranasal sinuses", Adv. Physiol. Educ., Mar. 2006, vol. 30, pp. 30-32, doi:10.1152/advan.00046.2005.
Lal, "Frontal Sinus Stenting Techniques", Medscape, Dec. 19, 2018, 13 pgs.
Patel, "Functional Endoscopic Sinus Surgery", Medscape, Dec. 9, 2020, 9 pgs.
Tessema, "Nasal Cavity Anatomy, Physiology, and Anomalies on CT Scan", Medscape, Mar. 12, 2019, 12 pgs.
Scharf et al., "Pressure Measurements in the Normal and Occluded Rabbit Maxillary Sinus", Laryngoscope, Jun. 1995, vol. 105, pp. 570-574.
Schoenen, "Sphenopalatine Ganglion Stimulation in Neurovascular Headaches", The Neuromodulation Frontier, 2016, vol. 29, pp. 106-116, DOI: 10.1159/000434661.
Slunder, "Etiology, Diagnosis, Prognosis and Treatment of Sphenopalatine Ganglion Neuralgia", Journal of the American Medical Association, Sep. 27, 1913, vol. LXI, No. 13, pp. 1201-1206, doi: 10.1001/jama. 1913.04350140117027.
Tepper et al., "Sphenopalatine Ganglion (SPG): Stimulation Mechanism, Safety and Efficacy (Supplemental Article)", American Headache Society, 2017, vol. 57, pp. 14-28, doi: 10.1111/head.13035.
Tewfik, "Trigeminal Nerve Anatomy", Medscape, Nov. 28, 2017, 1 pg.
Trifa et al., "Skull Base Forgotten Foramina: a CT Pictorial Review", European Society of Radiology, 2015, pp. 1-20, DOI: 10.1594/ecr2015/C-1224.
UPCN Health Care Providers, "Procedure Pterygopalatine Ganglion RF Treatment", Feb. 23, 2019, 4 pgs.
Vaezeafshar et al., "Barosinusitis: Comprehensive review and proposed new classification system", Allergy Rhinol, Oct. 2017, vol. 8, No. 3, pp. e109-e117, doi: 10.2500/ar.2017.8.221.
Viguri et al., "Migraine Care: Why and How to Block the Sphenopalatine Ganglion Nerve", May 14, 2018, 7 pgs.
Wu et al., "Negative Pressure Therapy in the Regeneration of the Sciatic Nerve Using Vacuum-Assisted Closure in a Rabbit Model", Medical Science Monitor, Feb. 29, 2018, vol. 24, pp. 1027-1033, DOI: 10.12659/MSM.906696.
Xiong et al., "Computational fluid dynamics simulation of airflow in the normal nasal cavity and paranasal sinuses", American Journal of Rhinology, Sep.-Oct. 2008, vol. 22, No. 5, pp. 477-482, doi: 10.2500/ajr.2008.22.3211.
Xiong et al., "Numerical flow simulation in the post-endoscopic sinus surgery nasal cavity", Medical Biology Engineering Comput., 2008, vol. 46, pp. 1161-1167, published online Aug. 26, 2008, DOI: 10.1007/s11517-008-0384-1.
Yadav et al., "Ossified pterygo-spinous ligament: incidence and clinico-anatomical relevance in the adult human skulls of North India", International Journal of Research in Medical Sciences, Aug. 2014, vol. 2, No. 3, pp. 847-851, DOI: 10.5455/2320-6012. ijrms20140806.
Yegin et al., "Vidian Canal Types and Dehiscence of the Bony Roof of the Canal: An Anatomical Study", Turkish Archives of Otorhinolaryngology, 2017, vol. 55, pp. 22-26, DOI: 10.5152/tao.2017. 2038.
Yentur et al., "Nervus Intermedius Neuralgia: An Uncommon Pain Syndrome with an Uncommon Etiology", Letters, Jun. 6, 2000, vol. 19, No. 6, pp. 407-408.
Zygmunt et al., "Methods of evaluation of autonomic nervous system", Arch. Med. Sci., Feb. 2010, vol. 6, No. 1, pp. 11-18, DOI 10.5114/aoms.2010.13500.
Abuzayed et al., "Pneumatization degree of the anterior clinoid process: a new classification", Neurosurg. Rev. 2010, vol. 33, pp. 367-374, DOI: 10.1007/S10143-010-255-8.
Acar et al., "Computed tomography evaluation of the morphometry and variations of the infraorbital canal relating to endoscopic surgery", Brazilian Journal of Otorhinolaryngology, 2017, vol. 580, 9 pgs., http://dx.doi.org/10.1016/j.bjor.2017.08.009.
Acar et al., "The anatomic analysis of the vidian canal and the surrounding structures concerning vidian neurectomy using computed tomography scans", Brazilian Journal of Otorhinolaryngology, 2017, pp. 1-8, https://doi.org/10.1016/j.bjorl.2017.11.008.
Akbas et al., "Sphenopalatine ganglion pulsed radiofrequency treatment in patients suffering from chronic face and head pain", Revista Brasileira de Anestesiologia, 2016, vol. 66, No. 1, pp. 50-54, published online Sep. 16, 2014, http://dx.doi.org/10.1016/j.bjane. 2014.06.001.
Al-Esawi et al., "Temporal Bone Hyperpneumatization and Tinnitus: Clinico-Radiological Evaluation Using CT Scan", The Journal of Global Radiology, Sep. 5, 2017, 7 pgs., DOI; 10.7191/jgr.2017. 1034.
American Headache Society, "The American Headache Society Position Statement on Integrating New Migraine Treatments Into Clinical Practice", The American Headache Society, 2019, vol. 59, pp. 1-18, doi:10.0000/head. 13456.
Anusha et al., "Anatomical variations of the sphenoid sinus and its adjacent structures: a review of existing literature", Surg. Radiol. Anat., 2014, vol. 36, pp. 419-427, published online Oct. 22, 2013, DOI: 10.1007/s00276-013-1214-1.
Baldea et al., "CT study of the sphenoid sinus pneumatization types", Romanian Journal of Rhinology, Mar. 2012, vol. 2, No. 5, pp. 17-30.
Battisti et al., "Barosinusitis", In: StatPearls [Internet], Treasure Island (FL): StatPearls Publishing; Jul. 10, 2020, 5 pgs.
Beule, "Physiology and pathophysiology of respiratory mucosa of the nose and the paranasal sinuses", GMS Current Topics in Otorhinolaryngology—Head and Neck Surgery, 2010, vol. 9, pp. 1-24.
Britt et al., "Assessment of a Statistical Algorithm for the Prediction of Benign Paroxysmal Positional Vertigo", Journal of the American Medical Association Otolaryngology—Head & Neck Surgery, Oct.

(56) References Cited

OTHER PUBLICATIONS 2018, vol. 144, No. 10, pp. 883-886, published online Aug. 30, 2018, doi 10.1001/jamaoto.2018.1657.

Budu et al., "The anatomical relations of the sphenoid sinus and their implications in sphenoid endoscopic surgery", Rom. J. Morphol. Embryol., 2013, vol. 54, No. 1, pp. 13-16.

Charakorn et al., "Chronic sphenoid rhinosinusitis: management challenge", Journal of Asthma and Allergy, Nov. 6, 2016, pp. 199-205.

Chen et al., "The Radiology of Referred Otalgia", AJNR, Nov.-Dec. 2009, vol. 30, pp. 1817-1823, DOI: 10.3174/ajnr.A1605.

Crespi et al., "Measurement and implications of the distance between the sphenopalatine ganglion and nasal mucosa: a neuroimaging study", The Journal of Headache and Pain, 2018, vol. 19, No. 14, pp. 1-10, published online Feb. 13, 2018, https://doi.org/10.1186/s10194-018-0843-5.

Davoodi et al., "Anatomical Variations of Neurovascular Structures Adjacent Sphenoid Sinus by using CT Scan", Pakistan Journal of Biological Sciences, 2009, vol. 12, pp. 522-525, DOI: 10.3923/pjbs.2009.522.525.

Delano et al., "Relationship of the Optic Nerve to the Posterior Paranasal Sinuses: A CT Anatomic Study", Am. J. Neuroradiol., Apr. 1996, vol. 17, pp. 669-675.

Eagle, "Sphenopalatine Ganglion Neuralgia", Archives of Otolaryngology, Jan. 1942, vol. 35, No. 1, pp. 66-84, doi:10.1001/archotol.1942.00670010067004.

Edinger et al., "The Foramen Ovale", Evolution, Dec. 1954, vol. 8, pp. 389-404.

Elkammash et al., "Variability in sphenoid sinus pneumatization and its impact upon reduction of complications following seller region surgeries", Egyptian Journal of Radiology and Nuclear Medicine, 2014, vol. 45, pp. 705-714, available online May 21, 2014.

Frank et al., "Quantification of airflow into the maxillary sinuses before and after functional endoscopic sinus surgery", International Forum of Allergy and Rhinology, Oct. 2013, vol. 3, No. 10, pp. 834-840, DOI: 10.1002/alr.21203.

Godley et al., "Update on the diagnostic considerations for neurogenic nasal and sinus symptoms: A current review suggest adding a possible diagnosis of migraine", American Journal of Otolaryngology—Head and Neck Medicine and Surgery, pp. 1-22, doi:10.1016/j.amjoto.2018.09.021.

Gonul et al., "MDCT evaluation of nasopalatine canal morphometry and variations: An analysis of 100 patients", Diagnostic and Interventional Imaging, 2016, vol. 97, pp. 1165-1172, http://dx.doi.org/10.1016/j.diii.2015.11.012.

Hamid et al., "Anatomic Variations of the Sphenoid Sinus and Their Impact on Trans-sphenoid Pituitary Surgery", Skull Base, 2008, vol. 18, No. 1, pp. 9-15, published online Nov. 6, 2007. DOI:10.1055/s-2007-992764.

Herzallah et al., "Endoscopic Identification of the Pharyngeal (Palatovaginal) Canal: An Overlooked Area", Journal of Neurological Surgery—Part B, 2012, vol. 73, No. 85, pp. 352-357, published online Aug. 7, 2012, DOI: http://dx.doi.org/10.1055/S-0032-1322798.

Hewaidi et al., "Anatomic Variation of Sphenoid Sinus and Related structures in Libyan Population: CT Scan Study", Libyan Journal of Medicine, Sep. 2008, vol. 3, No. 3, pp. 128-133 DOI: 10.4176/080307.

Hiremath et al., "Assessment of variations in sphenoid sinus pneumatization in Indian population: A multidetector computed tomography study", Neuroradiology & Head and Neck Imaging, 2018, vol. 28, Issue 3, pp. 273-279, DOI: 10.4103/ijri.IJRI_70_18.

Ho et al., "Sphenopalatine ganglion: block, radiofrequency ablation and neurostimulation—a systematic review", The Journal of Headache and Pain, 2017, vol. 18, No. 118, pp. 1-27, DOI: 10.1186/s10194-017-0826-y.

Ibrahim et al., "Anatomical Variations of Paranasal Sinuses Gender and Age Impact", Global Journal of Otolaryngology, Mar. 23, 2018, vol. 14, Issue 1, pp. 1-8, DOI: 10.19080/GJO.2018.14.555877.

Ivezic et al., "Resorption of gas trapped in the body cavities: comparison of alveolar and pleural space with inner ear and paranasal sinuses", Adv. Physiol. Educ., 2006, vol. pp. 30-32, doi:10.1152/advan.00046.2005.

Kastler et al., "Interventional Procedures Under CT Guidance in Pain Managements (Cementoplasty Excluded)", Interventional Neuroradiology, vol. 9 (Supp 2), 2003, pp. 67-73.

Kayalioglu et al., "Variations in sphenoid sinus anatomy with special emphasis on pneumatization and endoscopic anatomic distances", Neurosciences, Jan. 2005, vol. 10, No. 1, pp. 79-84.

Kikuta et al., "Repetitive Sinus-Related Symptoms May Accelerate the Progression of Chronic Maxillary Atelectasis", Case Reports in Otolaryngology, Jul. 3, 2017, vol. 2017, Article ID 4296195, 5 pgs., https://doi.org/10.1155/2017/4296195.

Kim et al., "Optic nerve changes in chronic sinusitis patients: Correlation with disease severity and relevant sinus location", PLoSOne, Jul. 10, 2018, vol. 13, No. 7, pp. 1-14, https://doi.org/10.1371/journal.pone.0199875.

Kimoto et al., "Influence of Barometric Pressure in Patients with Migraine Headache", Internal Medicine, 2011, vol. 50, pp. 1923-1928, DOI: 10.2169/internalmedicine.50.5640.

Kousoulis et al., "Excessive Paranasal Sinuses and Mastoid Aeration as a Possible Cause of Chronic Headache", Case Reports in Otolaryngology, Dec. 4, 2013, vol. 2013, Article ID 836064, 5 pgs., http://dx.doi.org/10.1155/2013/836064.

Lee, "The relationship of the medial roof and the posterior wall of the maxillary sinus to the sphenoid sinus: a radiologic study", Brazilian Journal of Otorhinolaryngology, 2017, vol. 83, No. 4, pp. 375-380, published online May 9, 2016, http://dx.doi.org/10.1016/j.bjorl.2016.04.007.

Lokwani et al., "Anatomical variations of sphenoid sinus on multidetector computed tomography and its usefulness in trans-sphenoidal endoscopic skull base surgery", International Journal of Research in Medical Sciences, Sep. 2018, vol. 6, No. 9, pp. 3063-3071, DOI:http://dx.doi.org/10.18203/2320-6012.ijrms20183645.

Loomba et al., "Radiofrequency Ablation of the Sphenopalatine Ganglion Using Cone Beam Computed Tomography for Intractable Cluster Headache", Pain Physician, 2016, vol. 19, pp. E1093-E1096.

Loring et al., "Gas Absorption from Frontal Sinuses", Arch. Otolaryngol., Jun. 1973, vol. 97, pp. 470-474.

Ness et al., "Increase of Intraocular Pressure After Topical Administration of Prostaglandin Analogs", Arch. Ophthalmol., Dec. 1999, vol. 117, pp. 1646-1649.

Okuma et al., "Examination of fluctuations in atmospheric pressure related to migraine", SpringerPlus, 2015, vol. 4, No. 790, pp. 1-4, DOI: 10.1186/s40064-015-1592-4.

Peris-Celda et al., "Nervus intermedius and the surgical management of geniculate neuralgia", Journal of Neurosurgery, Aug. 10, 2018, pp. 1-9, DOI: 10.3171/2018.3.JNS172920.

Policeni et al., "ACR Appropriateness Criteria Cranial Neuropathy", Journal of the American College of Radiology, 2017, vol. 14, pp. S406-S420, http://dx.doi.org/10.1016/j.jacr.2017.08.035.

Priyadarshini et al., "The Anatomical Variations in the Neurovascular Relations of the Sphenoid Sinus: An Evaluation by Coronal Computed Tomography", Turk Neurosurgery, 2015, vol. 25, No. 2, pp. 289-293, DOI: 10.5137/1019-5149.JTN.10638-14.0.

Rahmati et al., "Normal Variations of Sphenoid Sinus and the Adjacent Structures Detected in Cone Beam Computed Tomography", J. Dent Shiraz Univ. Med. Science, Mar. 2016, vol. 17, No. 1, pp. 32-37.

Reddy et al., "Pictorial essay: Anatomical variations of paranasal sinuses on multidetector computed tomography—How does it help FESS surgeons?", Indian Journal of Radiology and Imaging, Nov. 2012, vol. 22, Issue 4, pp. 317-324, DOI:10.4103/0971-3026.111486.

Reino, "Factors in the pathogenesis of tumors of the Sphenoid and Maxillary Sinuses: A Comprehensive Study", The Laryngoscope, Oct. 2000, vol. 110, pp. 1-38. (Presented in two parts).

(56) References Cited

OTHER PUBLICATIONS

Mortimer et al., "Peripheral Nerve and Muscle Stimulation", Neuroprosthetics Theory and Practices, Chapter 4, Feb. 2004, pp. 1-48, https://doi.org/10.1142/9789812561763_0020.

* cited by examiner

METHODS AND DEVICES FOR ALLEVIATING DISORDERS ASSOCIATED WITH SINUS CAVITIES

CROSS-REFERENCE TO RELATED APPLICATIONS

The current application claims priority to U.S. Provisional Application No. 62/965,294, entitled "Methods and Devices for Alleviating Disorders Associated With the Sphenoid Sinus" to Marc Richard Dean, filed Jan. 24, 2020, the disclosure of which is hereby incorporated by reference in its entirety.

FIELD OF THE DISCLOSURE

The present disclosure relates to medical treatments, and in particular methods and devices to alleviate disorders associated with sinus cavities, including the sphenoid sinus.

BACKGROUND OF THE DISCLOSURE

Many disorders and/or pathologies stem from issues with nerve stimulation, such as understimulation and overstimulation of such nerves, which can lead to various neuropathies and/or neuralgias. These pathologies include such things as optic neuropathy, autonomic disfunction, trigeminal neuralgia, and migraines among many other disorders. Current methods of treating nerve disorders and pathologies involve treating symptoms, such as pain. Further, these methods typically rely on treating an individual with pharmaceutical or pharmacologic compositions. In many instances, pharmacological treatments involve many complex issues caused by continual treatment over long periods and/or reliance on an individual to carry the pharmaceuticals, should symptoms arise spontaneously. Additionally, these methods fall short of solving underlying physiological conditions that give rise to nerve pathologies in an individual.

SUMMARY OF THE DISCLOSURE

This summary is meant to provide examples and is not intended to be limiting of the scope of the invention in any way. For example, any feature included in an example of this summary is not required by the claims, unless the claims explicitly recite the feature.

In one embodiment, a method for diagnosing chronic neurogenic sinusitis includes manipulating pressure within a sinus cavity of an individual, and assessing physiological effects in the individual.

In another embodiment, the method further includes detecting nerve signals in the individual.

In a still further embodiment, the detecting nerve signals uses at least one of the group consisting of: electromyography and electrocardiography.

In still another embodiment, the method further includes restricting an ostium of the sinus cavity by placing a restricting device in the ostium.

In a yet further embodiment, the restricting device is selected from the group consisting of a plug, a balloon, and a dam.

In yet another embodiment, the restricting device allows for the manipulation of pressure within the sphenoid sinus.

In a further embodiment again, the sinus cavity is the sphenoid sinus.

In another embodiment again, manipulating the pressure is accomplished using a syringe, a vacuum, or a bulb.

In a further additional embodiment, the method further includes measuring the pressure within the sinus cavity.

In another additional embodiment, a method of treating chronic neurogenic sinusitis includes navigating a dilating device to a sinus ostium of an individual and dilating the sinus ostium of the individual.

In a still yet further embodiment, the navigating step includes inserting a dilating device into a nostril and passing the dilating device through the nasal cavity.

In still yet another embodiment, the dilating step is accomplished using at least one of the following: calipers, a drill, a shaver, a piliating punch, a stanberger punch, thru-cut forceps, a balloon, and a sponge.

In a still further embodiment again, the navigating step is accomplished using an imaging technique.

In still another embodiment again, the imaging technique is selected from at least one of the following: a camera, an endoscope, a telescope, and an image guided surgery system.

In a still further additional embodiment, the navigating step utilizes an image guided surgery system selected from the group consisting of: Johnson & Johnson TruDi, Medtronic Fusion, Medtronic Stealthstation 7, Medtronic Stealthstation 8, Stryker CranialMap, Stryker NAV3i, Stryker Scopus Hybrid navigation, BrainLab ExacTrac, BrainLab Kick, BrainLab KickEM, BrainLab Curve, Fiagon Navigation System, ClaroNav Navient, ClaroNav Navident, Atracsys Sprytract 180, NDI Polaris Spectra, Collin Digipointur, Surgical Theater Surgical planner, EPED Irisclinic, Anke ASA-610V, Micromar Aimnav, Bramsys BMS-225N, Synaptive Brightmatter Guide, and Heelforce Excelim-04.

In still another additional embodiment, the dilating step dilates the sphenoid ostium to a size of at least 3 mm.

In a yet further embodiment again, the method of treating chronic baro-sinusitis further includes treating the sphenoid ostium.

In yet another embodiment again, the treating the sphenoid ostium step includes installing a stent in the sphenoid ostium.

In a yet further additional embodiment, the stent has a generally cylindrical frame defining an axial direction with openings on each end.

In yet another additional embodiment, the stent possesses a generally hourglass shape, wherein the openings possess larger diameters than the middle portion of the stent.

In a further additional embodiment again, the treating the sphenoid ostium step includes topically applying a medicine to or within the sphenoid sinus.

In another additional embodiment again, the medicine is selected from the group consisting of: anti-inflammatories, anti-convulsants, antidepressants, stimulants, biologics, protective agents, nutraceuticals, anti-hypertensives, analgesics, anti-microbials, and anti-reflux compounds.

In various embodiments, the methods can be performed on a living animal or on a non-living cadaver, cadaver head, simulator (e.g. with the body parts, tissue, etc. being simulated), anthropomorphic ghost, etc.

The foregoing and other objects, features, and advantages of the disclosed technology will become more apparent from the following detailed description, which proceeds with reference to the accompanying figures.

DETAILED DESCRIPTION OF THE DISCLOSURE

Turning now to the diagrams and figures, embodiments herein are directed to methods of diagnosing and/or treating migraines and other disorders associated with the sphenoid sinus. Some embodiments described herein are designed to alleviate issues with the sphenoid sinus through minimally invasive methods. Additional embodiments are directed to devices that can be implanted in the sphenoid sinus and/or the sphenoid sinus. Further embodiments are directed to methods to diagnose disorders associated with the sphenoid sinus.

Figure 1:
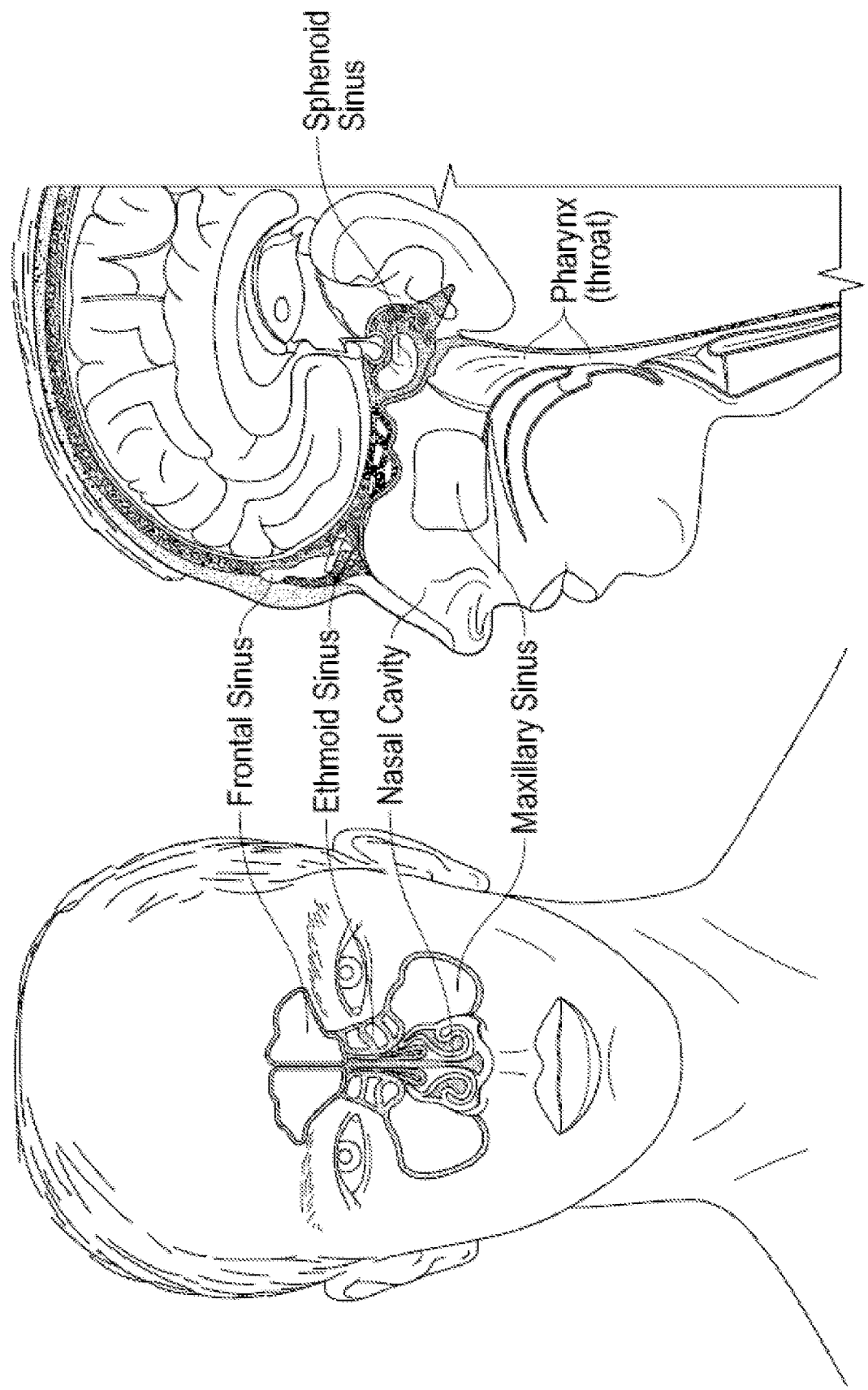
FIG. 1 illustrates frontal and side views of sinuses in a human in accordance with various embodiments.
Figure 2:
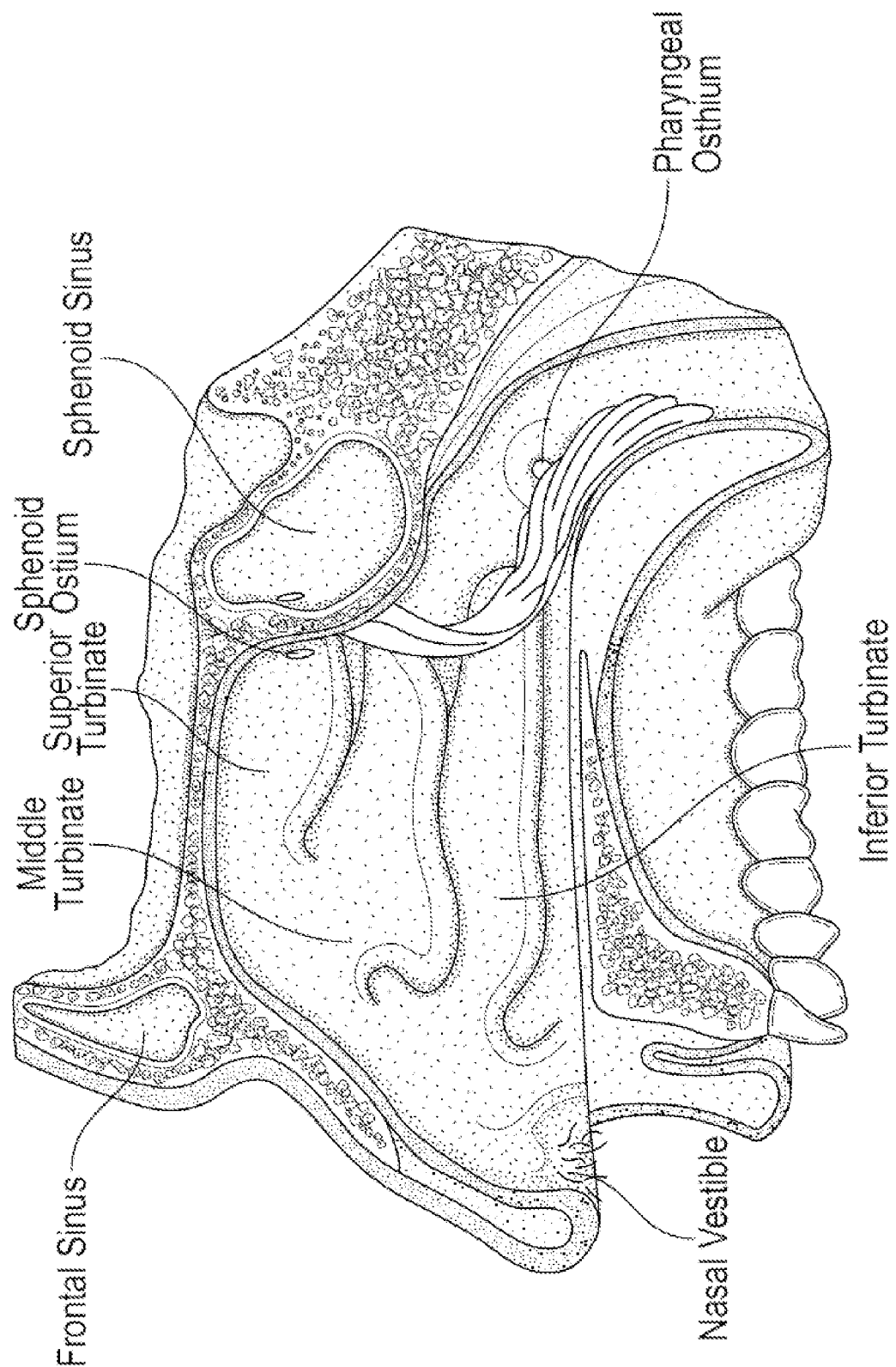
FIG. 2 illustrates a cross-sectional view of a human nasal cavity and sphenoid sinus in accordance with various embodiments.

Turning to FIG. 1, the sphenoid sinus is one of several sinuses that exist in the cranium of an individual, including the ethmoid sinuses, maxillary sinuses, and frontal sinuses. As seen in FIG. 2, the sphenoid sinus possesses an ostium that is typically medial to the superior turbinate, which allows for pressure regulation and ventilation of the sphenoid sinus. As individuals age, the sphenoid sinus pneumatizes. (See Scuderi et al., Amer. J. of Roentgenology, vol. 160, pp. 1101-04 (1993).) On average, the sphenoid ostium in humans is approximately 4 mm in diameter; however, many individuals possess ostia with openings approximately 1 mm or less. In some instances, individuals may possess ostia that are completely opacified or occluded (e.g., approximately 0 mm opening).

Figure 3A:
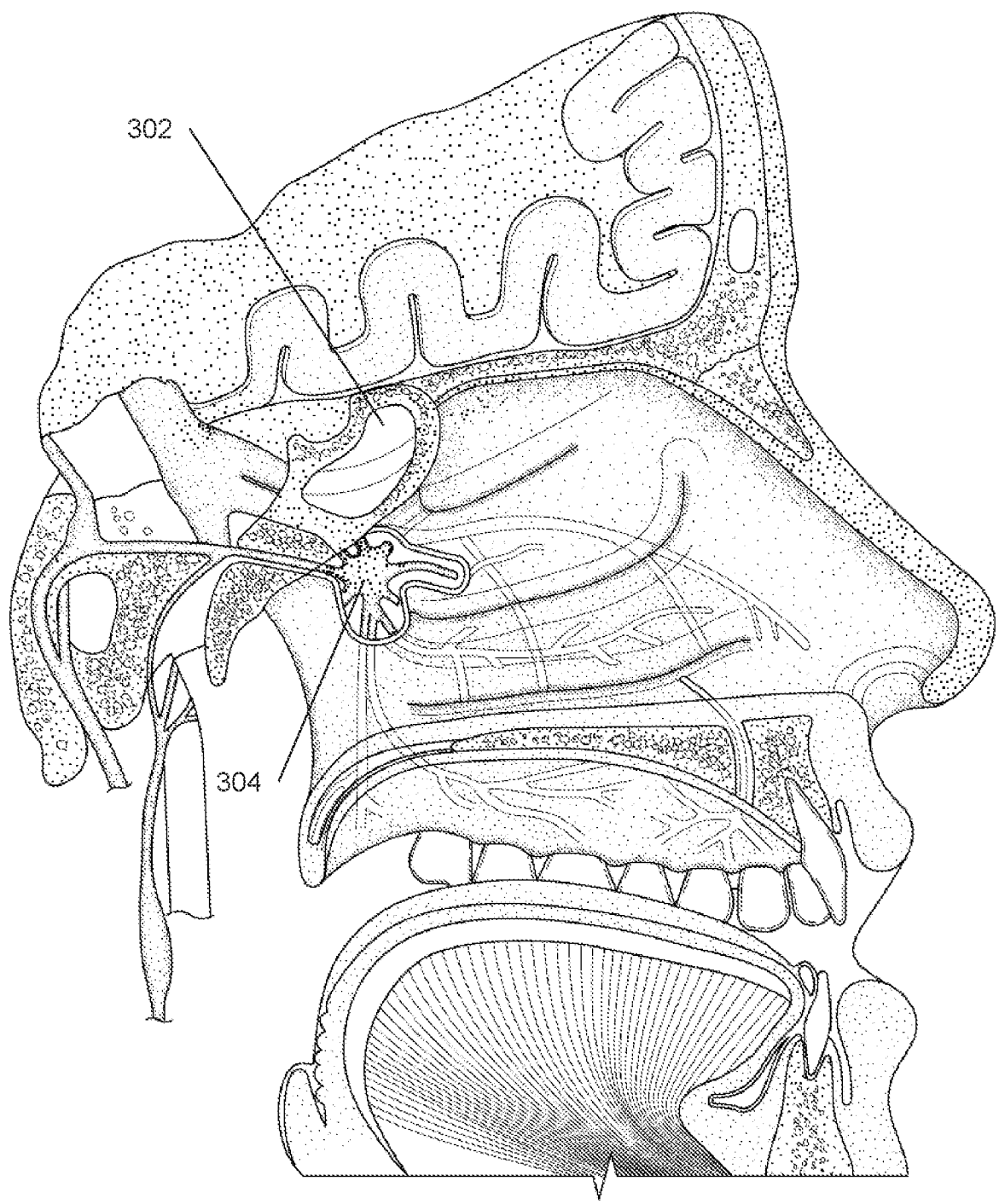
FIGS. 3A-3B illustrate cross-sectional views of the sphenoid sinus and sphenopalatine ganglion in relation to cranial anatomy in accordance with various embodiments.
Figure 3B:
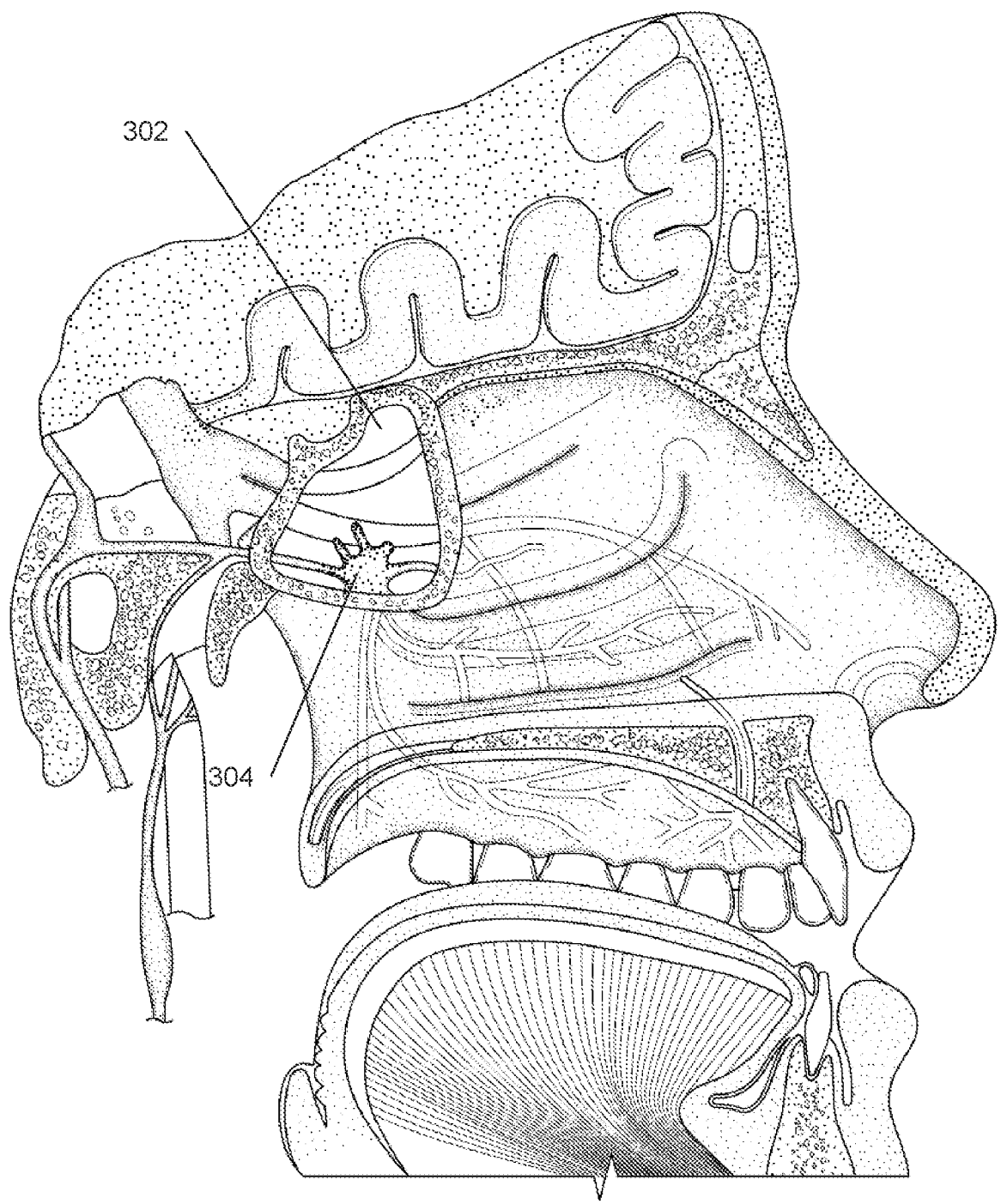

Turning to FIGS. 3A-3B, the sphenoid sinus 302 is surrounded by one of the largest collections of nerves, including the sphenopalatine ganglion 304 (also known as the pterygopalatine ganglion). Additionally, the sphenoid sinus is associated with the entirety or parts of the trigeminal nerve, vidian nerve; the optical nerve; cranial nerves II, III, IV, V, and VI; direct fibers from cranial nerves II-VII, IX, and X, as well as nerves associated with the autonomic and parasympathetic pathways. As illustrated in FIG. 3B, the pneumatization (e.g., hyperpneumatization) of the sphenoid sinus 302 in some individuals leads to some of the nerves, such as sphenopalatine ganglion 304 being located or exposed within the sphenoid sinus 302, thus allowing for injury and/or stimulation of these nerves. Stimulation of these nerves can result in physiological consequences, including pain (e.g., neuralgia); sensory effects, such as changes in vision, ability to smell, balance, etc.; and/or migraines. In some instances, exposure of the nerves can cause the nerves to be affected by pathologies affecting the sphenoid sinus 302, such as infections or inflammation.

Figure 4A:
FIGS. 4A-4D illustrate representations of medical imaging of sphenoid sinuses with normal and abnormal anatomies in accordance with various embodiments.

Turning to FIGS. 4A-4D, various exemplary representations of a sphenoid sinus are illustrated based on computerized tomography (CT) scans of individuals. FIG. 4A illustrates a coronal view of the sphenoid sinuses 402, 402' of an individual. While both sinuses show increased pneumatization, the left sphenoid sinus 402' (left in relation to patient's anatomy, right on figure) possesses a much higher level of pneumatization causing an increase in volume of the left sphenoid sinus 402'. Additionally, thinning of bone surrounding the left sphenoid sinus 402' leads to exposure of underlying nerves, including exposure of the vidian nerve 404, maxillary branch of trigeminal nerve 406, as well as a region 408 including CN III, CN IV, CN VI, ophthalmic branch $V_1$, and a region 410 containing the carotid artery. In contrast, the left sphenoid sinus 402 possesses no such thinning of the bone, thus possessing no exposed nerves or blood vessels.

Figure 4B:
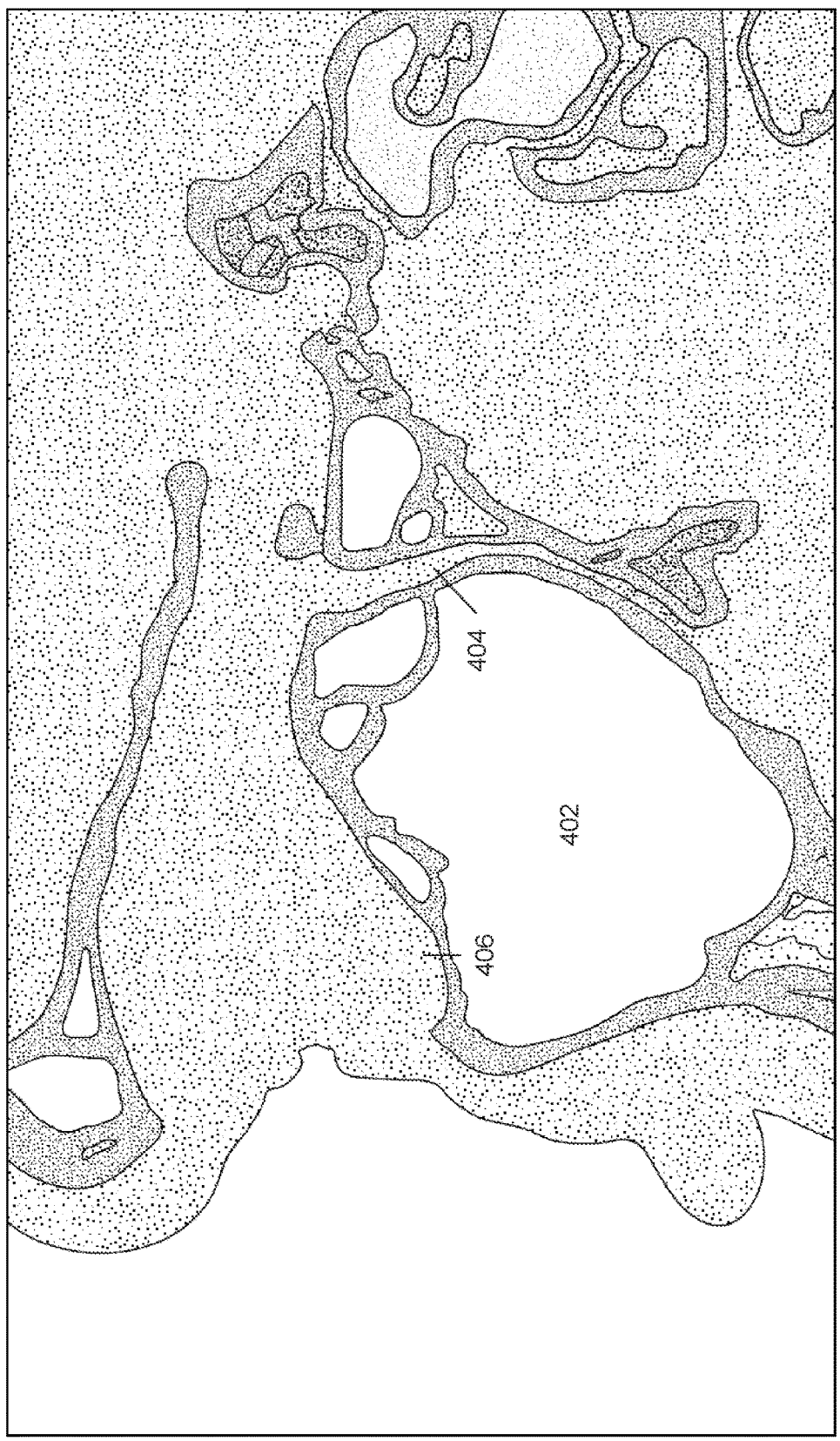
Figure 4C:
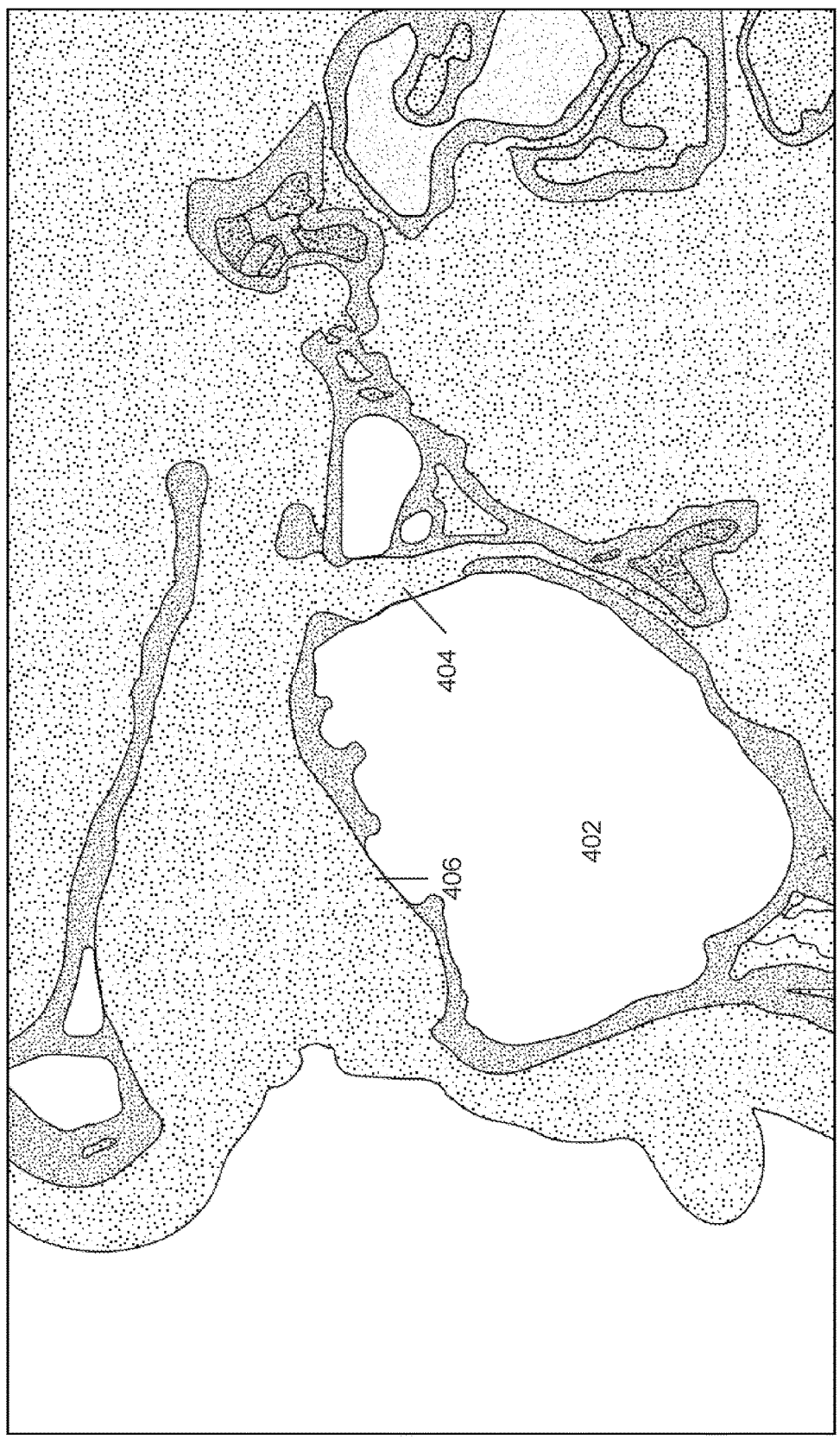

FIGS. 4B and 4C illustrate a sagittal view of maxillary sinus 402, where FIG. 4B illustrates an anatomically normal maxillary sinus, while FIG. 4C illustrates sinuses with thinning of the bone, leading to exposure of the sphenopalatine ganglion 404 and maxillary branch of trigeminal nerve 406, which are not exposed in an anatomically normal sinus of FIG. 4B.

Figure 4D:
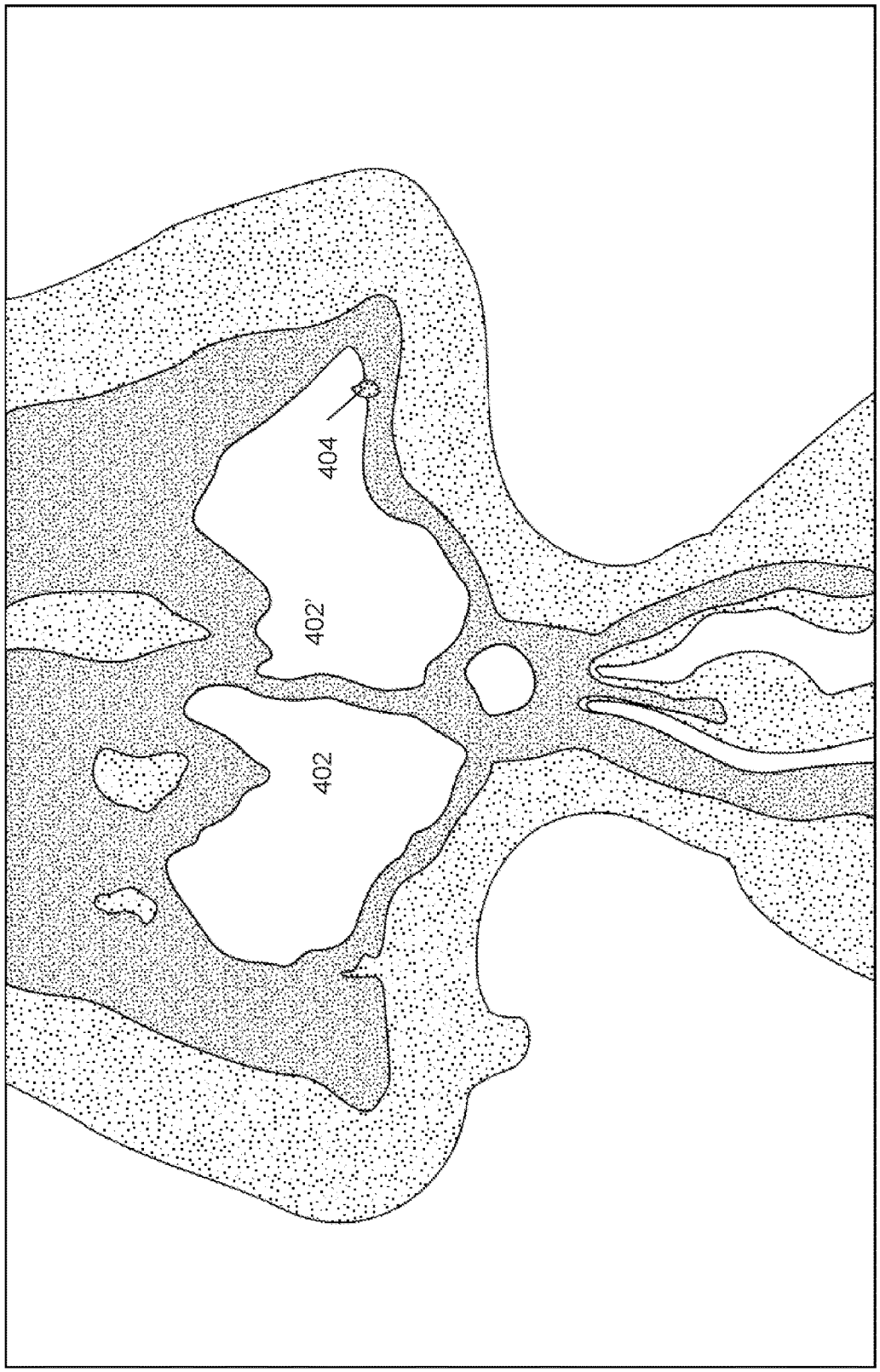

FIG. 4D illustrates a coronal view of the frontal sinuses 402, 402' of an individual. Due to pneumatization of the right frontal sinus 402', the ophthalmic branch of the trigeminal nerve 404 is exposed.

Besides anatomical variants, variations, or abnormalities with the sinus cavities, certain individuals may have abnormalities with the sinus ostium, such as a smaller than usual ostium, either congenital or acquired. A smaller ostium can prevent pressure normalization and ventilation within the sinus, thus creating an irregular pressure (e.g., different from the anatomical normal pressure) within the sinus. Additionally, the ostium of some individuals can become restricted and/or occluded, thus preventing pressure normalization and ventilation within the sinus. An increased pressure in the sinus places additional pressure on the nerves, while a decreased pressure can cause a vacuum surrounding one or more nerves into the sinus. In both increased and decreased pressure situations, the nerves can be stimulated, and potentially injured leading to one of the physiological conditions as noted above, including pain. Such pressure issues can be considered as neurogenic sinusitis and/or baro-sinusitis. Such conditions may be acute or chronic.

Identifying Chronic Neurogenic Sinusitis

Diagnosing chronic neurogenic sinusitis includes identifying individuals prone to irregular pressures in the sinus based on anatomical structure, including sinus pneumatization and/or ostium size. Diagnostic methods of some embodiments will identify individuals prone to chronic neurogenic sinusitis based on medical imaging of the sinus. Imaging methods that can be used in some embodiments include MRI, CT, PET, X-ray, and/or any other applicable medical imaging technique. In various embodiments, the resulting image is assessed for specific anatomical variations and/or abnormalities that indicate chronic neurogenic sinusitis. Some of the phenomena indicative of chronic neurogenic sinusitis include size of the sinus to identify the extent of pneumatization, where overly pneumatized sinuses can indicate the increased possibility of exposed nerves; bone dehiscence over nerve channels (e.g., foramen and/or fissures), which can expose the nerves and make the nerves susceptible to stimulation, injury, inflammation, and/or irritation; and/or any other anatomical phenomenon due to exposure of the nerves. Further embodiments identify other anatomical features, including the size of the ostium, such that a smaller ostium (caused by being boney or inflamed) indicating occlusion or an increased risk of occlusion, thus increasing the possibility of creating an abnormal pressure in the sphenoid sinus; and/or the size and/or location of the superior concha bullosa or supreme turbinate, which may occlude the ostium or increase the chance of occlusion from foreign objects and/or inflammation. Numerous embodiments image the nerves in and/or surrounding the sinus to identify the likelihood of exposure of these nerves to the sinus and/or dehiscence of the nerves into the sinus.

Additional embodiments of diagnostic imaging methods integrate algorithms, including artificial intelligence and/or machine learning techniques to automatically identify or detect the anatomical features of an individual, including the affected sinus, ostium, and/or any nerves present in the medical image. Additional embodiments determine the size and/or pneumatization of these anatomical features. Further embodiments calculate a risk and/or identify a diagnosis for the individual based on the anatomical features identified in the medical image. Various embodiments include more than one of the functions listed above, such that some embodiments identify and determine the size of anatomical features, while others will determine the size and assess a risk or determine a diagnosis for an individual. Several embodiments identify and determine the size of anatomical features and further assess a risk or determine a diagnosis for an individual.

Manual Methods of Diagnosing Chronic Neurogenic Sinusitis

Figure 5:
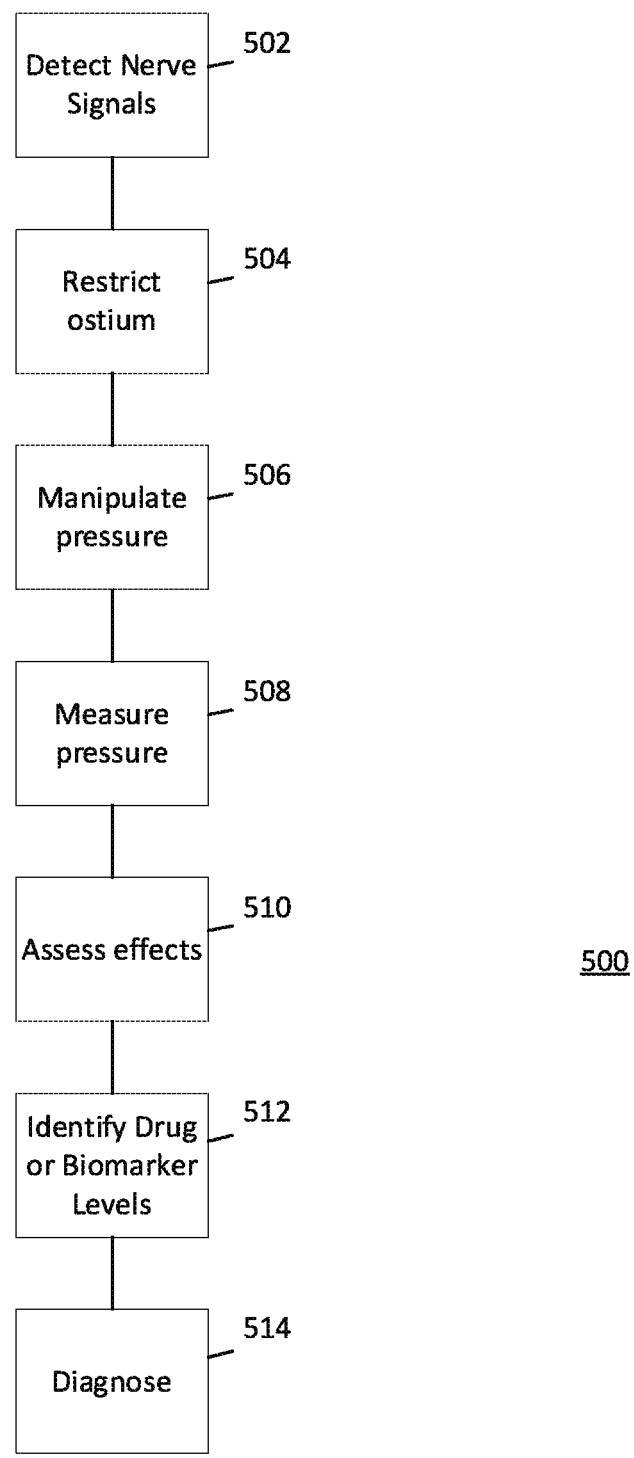
FIG. 5 illustrates a flow chart for a method of diagnosing chronic baro-sinusitis in accordance with various embodiments.

Additional embodiments of directed to methods of diagnosing and/or confirming chronic neurogenic sinusitis in an individual, such as an animal, human, cadaver, cadaver head, anthropomorphic ghost, and/or simulation/simulator. Turning to FIG. 5, method 500 illustrates features that can be used in such a diagnostic procedure. Additionally, while much of the discussion regarding FIG. 5 regards the sphenoid sinus, additional embodiments perform these methods on other sinus cavities throughout the head and body of an individual, including the frontal and maxillary sinus cavities. Given the teachings set forth herein, one of skill in the art would understand how to navigate to other sinus cavities and ostia. Additional embodiments directed to these other cavities also include additional methods to navigate to ostia as appropriate for a particular sinus.

In some of these embodiments, nerve signals are detected at 502. Certain embodiments detect nerve signals via neuromonitoring, such as electromyography (EMG), electrocardiography (ECG), and/or any other suitable method for neuromonitoring. At 502, one or more sensors (e.g., electrodes) are placed in a subject at locations relevant to the areas exhibiting pain or other physiological symptom or areas that are tied to one or more of the nerves located in the vicinity of the sphenoid sinus or order to assess nerve signal propagation stemming from a stimulus in the sphenoid sinus.

In many embodiments, the sphenoid ostium of a subject is artificially restricted at 404. A number of embodiments will restrict the ostium partially (e.g., allowing some of the ostium to remain open), while additional embodiments completely restrict (e.g., fully occlude) the ostium. In some embodiments, the restricting is accomplished by placing a restricting device, such as a plug, a balloon, a dam, a piece of cotton, or another obstruction placed in the ostium to prevent or restrict the pressure from normalizing within the sphenoid sinus. In certain embodiments, the restricting device allows for the manipulation of pressure within the sphenoid sinus using a syringe, a vacuum, a bulb and/or any other device capable of adding or removing a fluid, such as oxygen, nitrogen, air, or any other liquid or gas suitable for this purpose. Additional embodiments include a pressure gauge, vacuum gauge, or other instrument for measuring pressure in a system.

At 506, the pressure of the sphenoid sinus is manipulated in various embodiments. In some embodiments, the pressure is manipulated by allowing a restricting device or an occlusion to remain in place over time. When occluded, the pressure within the sphenoid sinus of many individuals will naturally begin to decrease, creating a negative pressure within the sphenoid sinus, or increase, creating a positive pressure within the sphenoid sinus. While in many embodiments, an individual, such as a doctor, manipulates the pressure using a syringe, a vacuum, a bulb and/or any other device capable of adding or removing a fluid, such as oxygen, nitrogen, air, or any other fluid (e.g., liquid or gas) suitable for augmenting pressure. In some embodiments, the pressure is reduced in the sphenoid sinus by removing some of the naturally occurring gas in the sphenoid sinus. In other embodiments, pressure is increased in the sphenoid sinus by adding a volume of a fluid, such as the fluids mentioned above, into the sphenoid sinus. In certain embodiments a doctor will augment the pressure in the sphenoid sinus by increasing then decreasing, or decreasing then increasing, pressure in the sphenoid sinus to test for the consequences of both increased and decreased pressure. In certain embodiments, the manipulation of pressure is accomplished by opening the sinus, such as by dilating an ostium or creating a new opening that normalizes pressure within the sinus and ambient or atmospheric pressure.

The pressure within the sphenoid sinus is measured at 508 of certain embodiments. At 508, an individual, such as a doctor or nurse, measures the pressure within the sphenoid sinus. The measurement can be obtained using a pressure gauge, vacuum gauge, or other instrument for measuring pressure in a system.

At 510 of many embodiments, physiological effects are assessed. In various embodiments, the physiological effects are assessed by querying a subject as to any feelings or issues they are feeling after occlusion of the ostium and/or manipulated pressure in the sphenoid sinus. In certain embodiments, EMG readings are measured from the electrodes, if EMG electrodes have been placed in an individual. Further embodiments actively stimulate one or more of the nerves in and/or exposed to the sphenoid sinus.

At 512, various embodiments identify drug levels or biomarkers present in the blood or other bodily fluid of the individual. Such drug levels include titer levels of analgesics, anti-inflammatories drugs (e.g., Non-steroidal anti-inflammatory drugs, opioids, steroidal anti-inflammatories), or any other drug level to control pain, pressure, inflammation, and/or any other symptom that may be associated with a nerve pain/issues or nervous system disorders. Biomarker levels include any native molecule that is associated with pain/issues or nervous system disorders, including calcitonin gene related peptide (CGRP) levels.

In certain embodiments, chronic neurogenic sinusitis is diagnosed at 514. In certain embodiments, physiological symptoms, including pain and/or nerve stimulation tied to an augmented or decreased pressure in the sphenoid sinus is assessed at this step. In many embodiments, the presence of pain or nerve stimulation is indicative of one or more exposed and/or dehiscent nerves in the sphenoid sinus that are susceptible to pressure changes in the sphenoid sinus. In such circumstances, chronic neurogenic sinusitis is identified as a cause of the symptoms in a subject. In certain embodiments, an individual, such as a doctor, may direct treatment for chronic neurogenic sinusitis through traditional methods or methods as described herein. Additionally, by identifying which nerves are affected by chronic barosinusitis allows a medical practitioner the ability to predict and/or treat specific nerves and/or auras that may be associated with a migraine. Additional embodiments utilize the levels of drugs and/or biomarkers present in blood or other bodily fluid to help form a diagnosis, where the inclusion of a drug may cause a dampening of particular symptoms, while the presence of certain biomarkers may indicate an increased likelihood of certain conditions, including nerve disorders, including possible nervous system disorders and/or migraines.

Figure 6:
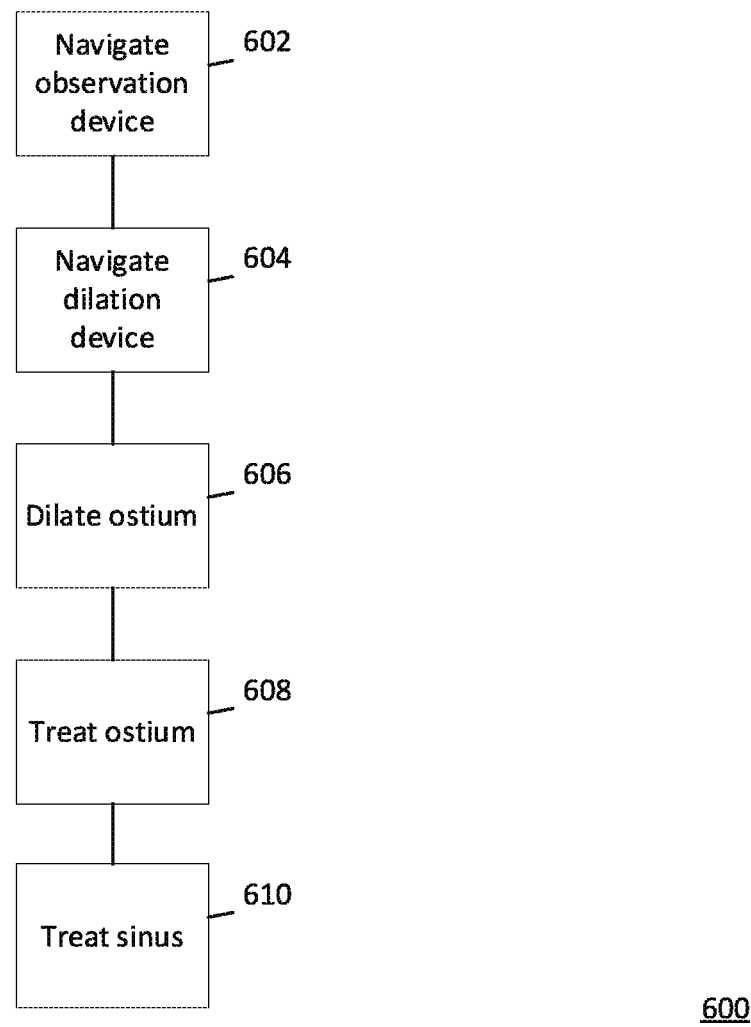
FIG. 6 illustrates a flow chart for a method of treating chronic baro-sinusitis in accordance with various embodiments.

The above features of the flow diagram of FIG. 5 may be executed or performed in an order or sequence beside the order and sequence shown and described in FIG. 6. Some of the above features of the flow diagram of FIG. 5 may be executed or performed substantially simultaneously where appropriate. Additionally, in some embodiments, some of the above features of the flow diagram of FIG. 5 may be omitted.

Treating Sinus Pathologies

To resolve acute or chronic neurogenic sinusitis (or barosinusitis) in many individuals, many embodiments dilate the sphenoid ostium to allow adequate pressure regulation in the sphenoid sinus in an individual, such as an animal, human, cadaver, cadaver head, anthropomorphic ghost, and/or simulation/simulator. Turning to FIG. 6, many embodiments are directed to minimally invasive methods to dilate a sinus ostium, such as method 600. Additionally, while much of the discussion regarding FIG. 6 regards the sphenoid sinus, additional embodiments perform these methods on other sinus cavities throughout the head and body of an individual, including the frontal and maxillary sinus cavities. Given the teachings set forth herein, one of skill in the art would understand how to navigate to other sinus cavities and ostia. Additional embodiments directed to these other cavities also include additional methods to navigate to and/or dilate ostia, including trephine, Caldwell-Luc, and any other procedures as appropriate for a particular sinus. Furthermore, the size to which a particular ostium is dilated for a particular sinus cavity may differ based on the particular sinus cavity, propensity of tissue in that area to heal, propensity of mucosal inflammation or infection, or other factors that may warrant larger or smaller dilations for a particular sinus than provided for the sphenoid sinus.

Several embodiments navigate an observation device to the sphenoid ostium at 602. In many embodiments, navigation involves inserting the observation device into the nostril and passing the dilating device through the nasal cavity (e.g., past the inferior, middle, and superior turbinates) to the sphenoid ostium. In certain embodiments, the observation device is inserted through the mouth and navigated into the nasal cavity through the connection in the throat. An observation device in accordance with some embodiments is used to observe and/or measure the ostium to identify an occluded or obstructed ostium and/or measure the ostial opening. In certain embodiments, the observation device is capable of imaging the sphenoid ostium and providing images (e.g., photographs and/or video) to a medical practitioner, such as a physician. In some embodiments, the images are live and/or real time images of the sphenoid ostium, while some embodiments obtain images and/or video to be viewed at a later time (e.g., stored for later viewing).

At 604, many embodiments navigate a dilating device to the sphenoid ostium. In numerous embodiments, the navigation step involves inserting the dilating device in the same or a similar manner as the observation device as described above regarding an observation device. In certain embodiments, the dilating device is attached to a catheter or other delivery device capable of navigating through the nasal cavity. Some embodiments utilize one or more imaging techniques to aid in navigating the dilating device to the sphenoid ostium, such as a camera on the delivery device, an endoscope, a telescope, an image guided surgery system (IGS) (optical and/or electromagnetic), such as Johnson & Johnson's TruDi system; Medtronic's Fusion or Stealthstation systems (e.g., Stealthstation 7, Stealthstation 8, etc.), Stryker's CranialMap, Scopus Hybrid navigation, or NAV3i; or BrainLab's ExacTrac, Kick, KickEM, or Curve systems; Fiagon's Navigation System; ClaroNav's Navient or Navident systems; Atracsys' Sprytract 180; NDI's Polaris Spectra; Collin's Digipointur; Surgical Theater's Surgical planner; EPED's Iris-clinic; Anke's ASA-610V; Micromar's Aimnav; Bramsys' BMS-225N; Synaptive's Brightmatter Guide; and/or Heelforce's Excelim-04.

In many embodiments, the dilating device is selected from one or more of the following: calipers, a drill, a shaver, a piliating punch, a stanberger punch, thru-cut forceps, a balloon, a sponge, and/or any other device capable of cutting or expanding a hole in the sphenoid ostium.

Once the dilating device is located at the sphenoid sinus ostium, the sphenoid ostium is dilated in accordance to the type of dilating device in many embodiments. For example, when using a drill, the drill bit is inserted through the ostium while spinning to allow the ostium to increase in size as the drill bit pass through the ostium. Additionally, a punch is pushed through tissue (e.g., bone, mucosa, etc.) to expand ostial size in embodiments using a punch. In embodiments using a balloon, the balloon is inserted through the ostium in a deflated state, then the balloon is inflated, thus expanding the size of the sphenoid ostium. It should be noted that the above examples are only exemplary, and a qualified medical professional will understand the best techniques of use for the specific dilating device being used to expand the ostium.

Additionally, in many embodiments, the sphenoid ostium is dilated to a size sufficient to allow pressure normalization of the sphenoid sinus and/or prevent occlusion of the sphenoid ostium at 606. In some embodiments, the sphenoid ostium is dilated to the typical average size of approximately 4 mm (±0.5 mm), while some embodiments dilate the ostium to a size sufficient to allow pressure normalization within the sphenoid sinus. As such, certain embodiments dilate the ostium to approximately 3 mm, 4 mm, 5 mm, 6 mm, or greater. Certain embodiments dilate the ostium to a size approximately double the intended ostium size in case swelling, inflammation, scar tissue formation, or any other phenomenon that may occlude or obstruct the ostium post dilation. For example, if 4 mm is the desired or intended size, the ostium is dilated to approximately 8 mm to allow the ostium to remain at least approximately 4 mm after healing. As such, certain embodiments dilate the ostium to approximately, 8 mm, 10 mm, 12 mm, 14 mm, 16 mm, or greater.

In some embodiments, the time and/or pressure of the dilation step is altered to provide histological benefit, when using a balloon or similar dilating device. For example, dilating the ostium with a balloon for a period of time and at a particular pressure may help stabilize the mucosa within the ostium and/or prevent further inflammation of the mucosa in the future. In some embodiments, the dilating step inflates a balloon for up to about 10 minutes (±1 minute) before releasing pressure from the balloon. Specifically, certain embodiments maintain the balloon inflated for about 1 minute, about 2 minutes, about 3 minutes, about 4 minutes, about 5 minutes, about 6 minutes, about 7 minutes, about 8 minutes, about 9 minutes, or about 10 minutes. Additionally, several embodiments inflate the balloon to a pressure of up to about 15 atmospheres (atm) (±1 atm), depending on efficacy or need of a pressure to dilate or maintain dilation. Specifically, certain embodiments inflate the balloon to about 5 atm, about 6 atm, about 7 atm, about 8 atm, about 9 atm, about 10 atm, about 11 atm, about 12 atm, about 13 atm, about 14 atm, or about 15 atm. In combination, embodiments utilize different combinations of time and pressure to achieve the desired results. For example, if a 2-minute inflation at 12 atm is shown to show the desired results, some embodiments may inflate to a lower pressure for a longer time to achieve similar results (e.g., 10 atm for 3 minutes).

Further embodiments treat the sphenoid ostium to maintain the ostial opening at 608. In certain embodiments, a mechanical device, such as a stent, is used to prevent an ostium from closing such as from a healing process or formation of scar tissue. In certain embodiments, a topical application of a medicine is used to treat the tissue in the ostium to prevent inflammation and/or tissue growth, which may obstruct or occlude the ostium after dilation. For example, anti-inflammatories (e.g., steroids, NSAIDs), anti-convulsants (e.g., gabapentin, sumatriptan), antidepressants (e.g., SSRIs); stimulants (e.g., caffeine, epinephrine); biologics, including anti-CGRP drugs (e.g., Aimovig, Ajovy, Emgality, and Dupixent); protective agents (e.g., Carafate, petroleum jelly), nutraceuticals, (e.g., curcumin, willow bark extract, CBD), anti-hypertensives (e.g., alpha- and beta-blockers, calcium channel blockers), analgesics (e.g., lidocaine, benzocaine), anti-microbials (e.g., antibiotics, antivirals, antifungals), anti-reflux compounds (e.g., PPIs, $H_2$ blockers) and/or any other drug producing the desired effect, or a combination thereof can be applied to the dilated ostium to prevent closure of the ostium. In certain embodiments, the drug is applied to the dilating device directly, such that 608 occurs simultaneously with 606.

A stent in accordance with some embodiments forms a generally cylindrical frame defining an axial direction with openings on each end. In some embodiments, the stent is collapsible and expandable for delivery using a balloon catheter or encapsulated within a sheath catheter. In other embodiments, the stent is rigid and is inserted into an ostium. In numerous embodiments, the stent is made of a biocompatible material. In some embodiments the frame is a suitably long enough such that one opening is in the sphenoid sinus, while the other end remains in the nasal cavity. In numerous embodiments, the diameter of the stent matches the size of the ostium, such that the diameter is approximately 3 mm, 4 mm, 5 mm, 6 mm, or greater. In some embodiments, the diameter of the stent may exceed the size of the ostium in order to secure the stent in the ostium.

The stent of many embodiments is constructed of a stable and biocompatible material for permanent installation, or planned removal in the future after installation, such as some metals and/or plastics. For example, the stent can be manufactured from one or more of the following materials: stainless steel, a nickel-based alloy (e.g., a cobalt-chromium or a nickel-cobalt-chromium alloy), Nitinol, certain polymers, any other biocompatible material, and/or combinations thereof.

In several embodiments, the stent is constructed of a bioabsorbable or biodegradable material, such that the stent will eventually break down and not remain as a foreign body in an individual. Examples of bioabsorbable materials include poly(L-lactide) (PLLA), poly(D-lactide) (PDLA), polyglycolide (PGA), poly(L-lactide-co-glycolide) (PLGA), polyhydroxyalkonate (PHA), polysaccharides, proteins, polyesters, polyhydroxyalkanoates, polyalkelene esters, polyamides, polycaprolactone, polylactide-co-polycaprolactone, polyvinyl esters, polyamide esters, polyvinyl alcohols, modified derivatives of caprolactone polymers, polytrimethylene carbonate, polyacrylates, polyethylene glycol, hydrogels, photo-curable hydrogels, terminal dials, poly (L-lactide-co-trimethylene carbonate), polyhydroxybutyrate; polyhydroxyvalerate, poly orthoesters, poly anhydrides, poly immocarbonates, and copolymers and combinations thereof.

Further embodiments of stents also have elements of maintaining the position in the sphenoid ostium. Some embodiments possessing these elements will include tissue engaging elements capable to allow fixation of the stent to the wall of the sphenoid ostium. The tissue engaging elements can be any number of shapes, including barbs, coils, and/or arrowheads. Numerous embodiments may shape the stent into an hourglass shape that the openings possess larger diameters than the middle portion of the stent. In this configuration, the larger diameters of the openings will prevent the stent from moving into or out of the sphenoid ostium.

It should be noted that embodiments may possess one or more of the above features, such as certain embodiments may possess more than one of an hourglass shape, tissue engaging elements, and/or constructed of various biocompatible materials.

Additionally, certain embodiments involving a stent will further include a drug impregnated into the stent, such as the drugs described above to prevent closing of the ostium. Including a drug impregnated with the stent can allow for a controlled release of the drug over time, or it could be a fast-acting drug to be applied for only temporary application to the ostium.

At 610, many embodiments will treat to the interior of the sphenoid sinus to alleviate pain or other consequences from nerve stimulation due to chronic baro-sinusitis. In certain embodiments, the treatment is a physical (e.g., non-drug) treatment method, while additional embodiments will apply a drug to the interior of the sphenoid sinus. Some embodiments utilize a combination of physical and drug-based treatments to the interior of the sphenoid sinus. In many embodiments, the treatment will be temporary to alleviate symptoms without long term effects, while some embodiments utilize permanent methods to alleviate symptoms. In a number of embodiments, the treatment utilizes both temporary and permanent treatments to alleviate symptoms, such as to permanently block stimulation of some nerves but only temporarily block stimulation of certain nerves.

Physical methods include ablation, irreversible electrophoresis (IRE), light therapy, targeted radiation, signal modulation, stimulating a nerve in a reflex arc to prevent stimulation of an overstimulated nerve, increasing the stimulation of an understimulated or non-stimulated nerve, or stimulating a nerve that is understimulated due to damage or other pathology. Drug-based methods include the application of one or more of an anti-inflammatory (e.g., steroids, NSAIDs), an anti-convulsant (e.g., gabapentin, sumatriptan), an antidepressant (e.g., SSRIs); a stimulant (e.g., caffeine, epinephrine); a biologic, including an anti-CGRP, (e.g., Aimovig, Ajovy, Emgality, and Dupixent); a protective agent (e.g., Carafate, petroleum jelly), a nutraceutical, (e.g., curcumin, willow bark extract, CBD), an anti-hypertensive (e.g., alpha- and beta-blockers, calcium channel blockers), an analgesic (e.g., lidocaine, benzocaine), an anti-microbial (e.g., antibiotics, antivirals, antifungals), an anti-reflux compound (e.g., PPIs, $H_2$ blockers) and/or any other drug producing the desired effect, or a combination thereof. In many embodiments, drug treatments are topically applied to the nerve. Topically treating the nerve directly provides the benefits of direct targeting of the nerve of issue, which can allow lower doses of the drug as well as fewer systemic side effects caused by traditional methods of oral, intravenous, or any other method of treating symptoms using some drugs. Furthermore, various embodiments apply the drug via a balloon or other drug reservoir to allow for topical and regulated release of the drug.

The above features of the flow diagram of FIG. 6 may be executed or performed in an order or sequence beside the order and sequence shown and described in FIG. 6. Some of the above features of the flow diagram of FIG. 6 may be executed or performed substantially simultaneously where appropriate—for example, some embodiments may utilize a combination observation and dilation device, where the ostium is imaged followed immediately by dilation and/or treatment without a second navigation step. Additionally, in some embodiments, some of the above features of the flow diagram of FIG. 6 may be omitted.

Treating Additional Disorders

It should be noted that the above example to treat chronic neurogenic sinusitis is only one disorder, and these embodiments of these devices and methods can also be used to treat other, similar phenomena in an individual. For example, nerves in the ear (including the facial, vestibular, and cochlear nerves) may also be associated with pain or other physiological effect caused by abnormal pressures in the middle ear cavities. As such, some embodiments are directed to modifying the Eustachian tube to allow improved pressure normalization and/or regulation in the middle ear to alleviate pressure on the dura, cochlea, semicircular canals, carotid artery, round window, facial nerve, nervus intermedius, geniculate ganglion, Jacobson's nerve, Arnold's nerve, nerve to the stapedius, tympanic plexus, erichlear branch of the trigeminal nerve, and/or chorda tympani. It should be noted that a doctor or physician would be knowledgeable how to adjust the methods described above to allow for pressure regulation and/or normalization within the ear.

Additionally, other pneumatized cavities throughout the body, including (but not limited to) pneumatized cavities in the head, including the maxillary, frontal, and ethmoid sinuses, as well as concha bullosa, may also be associated with nerves and pain or other physiological effect associated with abnormal pressures in those sinuses. Several embodiments herein are directed to dilating or creating ostia or other openings in these other sinuses to regulate and/or normalize pressures within these sinuses. A physician or other medical professional will be able to modify techniques and embodiments described above to obviate or alleviate physiological effects associated with the abnormal pressures within these other sinuses, including the use of certain gas compositions (e.g., oxygen, nitrogen, heliox, air, etc.).

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

The invention claimed is:

1. A method for diagnosing chronic neurogenic sinusitis comprising:
    manipulating a barometric pressure within a sinus cavity of an individual, wherein manipulating the barometric pressure comprises:
        occluding all ostia associated with the sinus cavity; and
        changing the barometric pressure within the sinus cavity;
    wherein the individual suffers from one or more of neuropathy and neuralgia; and
    assessing the one or more of neuropathy and neuralgia of the individual, wherein a change of severity of at least one of the one or more of neuropathy and neuralgia due to the manipulated barometric pressure indicates the individual possesses neurogenic sinusitis, wherein neurogenic sinusitis is characterized by a stimulation of at least one nerve due to an abnormal barometric pressure within the sinus cavity.

2. The method of claim 1, further comprising detecting nerve signals in the individual.

3. The method of claim 2, wherein the detecting nerve signals uses at least one of the group consisting of: electromyography and electrocardiography.

4. The method of claim 1, wherein occluding all ostia comprises placing a restricting device in an ostium.

5. The method of claim 4, wherein the restricting device is selected from the group consisting of a plug, a balloon, and a dam.

6. The method of claim 4, wherein the restricting device allows for the manipulation of the gas pressure within a sinus cavity.

7. The method of claim 1, wherein the sinus cavity is the sphenoid sinus, and the nerve is selected from: the trigeminal nerve, the vidian nerve, the optical nerve, cranial nerve II, cranial nerve III, cranial nerve IV, cranial nerve V, cranial nerve VI, cranial nerve VII, cranial nerve IX, and cranial nerve X.

8. The method of claim 1, wherein changing the barometric pressure is accomplished using a syringe, a vacuum, or a bulb.

9. The method of claim 1, further comprising measuring the barometric pressure within the sinus cavity.

10. The method of claim 1, wherein the neuropathy and neuralgia include one or more of: pain; changes in vision, changes in ability to smell, changes in balance, and migraine.

11. The method of claim 1, wherein the at least one nerve is exposed due to hyperpneumatization of the sinus cavity.

12. The method of claim 1, wherein changing the barometric pressure comprises compressing a gas within the sinus cavity.

13. The method of claim 1, wherein the sinus cavity comprises no more than one ostium.

14. The method of claim 1, wherein changing the barometric pressure comprises altering gas composition within the sinus cavity.

15. The method of claim 1, wherein the sinus cavity is selected from the group consisting of: a sphenoid sinus, an ethmoid sinus, a maxillary sinus, a frontal sinus, and a middle ear cavity.

16. The method of claim 1, wherein the nerve is selected from the group consisting of: a facial nerve, a nervus intermedius, a geniculate ganglion, a Jacobson's nerve, an Arnold's nerve, a nerve to the stapedius, a tympanic plexus, an erichlear branch of the trigeminal nerve, and a chorda tympani.

17. A method of treating chronic neurogenic sinusitis comprising:
  manipulating a barometric pressure within a sinus cavity of an individual, wherein manipulating the barometric pressure comprises:
    occluding all ostia associated with the sinus cavity; and
    changing the barometric pressure within the sinus cavity;
    wherein the individual suffers from one or more of neuropathy and neuralgia;
  assessing the one or more of neuropathy and neuralgia of the individual, wherein a change of severity of at least one of the one or more of neuropathy and neuralgia due to the manipulated barometric pressure indicates the individual possesses neurogenic sinusitis, wherein neurogenic sinusitis is characterized by a stimulation of at least one nerve due to an abnormal barometric pressure within the sinus cavity; and
  dilating the sinus ostium of the individual to at least 3 mm, wherein dilating the sinus ostium relieves the abnormal barometric pressure within the sinus cavity, wherein relieving the abnormal barometric pressure within the sinus cavity alleviates at least one of the one or more of neuropathy and neuralgia.

18. The method of claim 17, wherein the dilating step is accomplished using at least one of the following: calipers, a drill, a shaver, a piliating punch, a stanberger punch, thru-cut forceps, a balloon, and a sponge.

19. The method of claim 17, further comprising installing a stent in the dilated sinus ostium, wherein the stent possesses:
  a generally cylindrical frame defining an axial direction with openings on each end, or
  a generally hourglass shape, wherein the openings possess larger diameters than the middle portion of the stent.

20. The method of claim 19, wherein the stent maintains the dilated ostium to normalize the gas pressure within the sinus cavity.

21. The method of claim 17, further comprising topically applying a medicine to the sinus cavity.

22. The method of claim 21, wherein the medicine is selected from the group consisting of: anti-inflammatories, anti-convulsants, antidepressants, stimulants, biologics, protective agents, nutraceuticals, anti-hypertensives, analgesics, anti-microbials, and anti-reflux compounds.

23. The method of claim 17, wherein the at least one nerve is exposed due to hyperpneumatization of the sinus cavity.

24. The method of claim 17, wherein the sinus ostium is dilated to at least 6 mm, such that the ostium size remains at least 3 mm after healing.

25. The method of claim 17, wherein the sinus cavity comprises no more than one ostium.

26. The method of claim 17, further comprising navigating a dilating device to a sinus ostium of an individual.

27. The method of claim 26, wherein the navigating step is accomplished using an imaging technique.

28. The method of claim 27, wherein the imaging technique is selected from at least one of the following: a camera, an endoscope, a telescope, MRI, CT, PET, X-ray and an image guided surgery system.

29. The method of claim 26, wherein the navigating step comprises:
  inserting a dilating device into a nostril; and
  passing the dilating device through the nasal cavity.

30. The method of claim 26, wherein the navigating step utilizes an image guided surgery system selected from the group consisting of: Johnson & Johnson TruDi, Medtronic Fusion, Medtronic Stealthstation 7, Medtronic Stealthstation 8, Stryker CranialMap, Stryker NAV3i, Stryker Scopus Hybrid navigation, BrainLab ExacTrac, BrainLab Kick, BrainLab KickEM, BrainLab Curve, Fiagon Navigation System, ClaroNav Navient, ClaroNav Navident, Atracsys Sprytract 180, NDI Polaris Spectra, Collin Digipointur, Surgical Theater Surgical planner, EPED Iris-clinic, Anke ASA-610V, Micromar Aimnav, Bramsys BMS-225N, Synaptive Brightmatter Guide, and Heelforce Excelim-04.

* * * * *